United States Patent [19]

Dyroff et al.

[11] Patent Number: 4,824,591

[45] Date of Patent: Apr. 25, 1989

[54] SULFONE PEROXYCARBOXYLIC ACIDS

[75] Inventors: David R. Dyroff; Daniel P. Getman; Joan K. Glascock, all of St. Louis, Mo.

[73] Assignee: Monsanto Company, St. Louis, Mo.

[21] Appl. No.: 168,033

[22] Filed: Mar. 14, 1988

Related U.S. Application Data

[60] Division of Ser. No. 97,274, Sep. 17, 1987, Pat. No. 4,758,369, which is a continuation-in-part of Ser. No. 962,592, Nov. 3, 1986, abandoned.

[51] Int. Cl.$^4$ .................. C11D 3/39; C11D 7/38
[52] U.S. Cl. .......................... 252/94; 252/95; 252/99; 252/135; 252/186.23; 252/186.42; 8/111; 260/502 R
[58] Field of Search ............... 252/94, 95, 99, 100, 252/135, 186.23, 186.42; 8/111; 260/502 R

[56] References Cited

U.S. PATENT DOCUMENTS

| | | |
|---|---|---|
| 3,847,830 | 11/1974 | Williams et al. ............ 252/186 |
| 4,094,808 | 6/1978 | Stewart et al. ............ 252/186 |
| 4,100,095 | 7/1978 | Hutchins et al. ............ 252/99 |
| 4,321,301 | 3/1982 | Brichard et al. ............ 428/99 |
| 4,681,592 | 7/1987 | Hardy et al. ............ 252/95 |

FOREIGN PATENT DOCUMENTS 0105690  4/1984  European Pat. Off. .

OTHER PUBLICATIONS

Barbieri et al., La Ricerca Scientifica, 33 Rendiconti A3, No 8 Series 2, 1233–1235 (1963).
Barbieri et al., Bollenttino 23, 47–52 (1965).
Folli et al., J. Chem Soc. (1968) (11), 1317–1322.
Folli et al., Bollentino, 26, 61–69 (1968).

*Primary Examiner*—Paul Lieberman
*Assistant Examiner*—Hoa Van Le
*Attorney, Agent, or Firm*—R. Loyer; A. Cole; R. Shear

[57] ABSTRACT

There are disclosed novel, highly stable sulfone peroxycarboxylic acids useful in detergent compositions alone or as bleaching agents which are represented by the formula

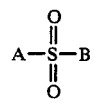

wherein A and B are organic moieties bonded to the sulfur atom by a carbon atom and at least one of A and B containing at least one

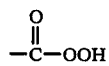

group bonded to a carbon atom.

62 Claims, No Drawings

SULFONE PEROXYCARBOXYLIC ACIDS

This is a division of application Ser. No. 097,274, filed Sept. 17, 1987 now U.S. Pat. No. 4,758,369 which is a continuation-in-part of application Ser. No. 962,592 filed Nov. 3, 1986, now abandoned.

This invention relates to dry, stable bleaches comprising a sulfone peroxycarboxylic acid having a sulfone group and attached thereto organic moieties containing at least one peroxycarboxylic acid group.

BACKGROUND OF THE INVENTION

The present invention relates to dry, stable bleaching compositions comprising a sulfone peroxycarboxylic acid compound having surprising inherent properties providing active oxygen bleaching performance even after long storage periods.

The property possessed by some materials to bleach is known and widely used to remove discoloration or stains from articles. The behavior and mechanisms by which such bleaching agents perform their functions are only partially understood. It is known that many colored materials contain a conjugated chain, that is, a series of double bonds which alternate with single bonds. If one of the double bonds is eliminated the color is usually destroyed. Therefore, an agent which will remove a double bond linkage may be an effective bleach. A bleaching agent may also act on the groups at the end of the chain. Bleaching materials are generally categorized as chlorine, hypochlorites, chloramines, hydrogen peroxide and other peroxy compounds, chlorite and chorine dioxide and reducing agents.

One well known category of bleaches comprises active chlorine releasing compounds. Bleaches in this category, while effective, have the disadvantages of tending to weaken or degrade fabrics or other materials, to react with other components of formulations containing them, to degrade the colors of many dyed fabrics or other colored articles and to cause yellowing of some synthetic or resin treated fabrics, etc.

The disadvantages of the active chlorine releasing bleaches are largely overcome by a second known category of bleaches referred to as inorganic oxygen bleaches comprising inorganic active oxygen releasing compounds. Bleaches in this category, while effective, have also exhibited significant disadvantages. For example, inorganic oxygen bleaches such as hydrogen peroxide, sodium perborate, sodium percarbonate, and the like, while often possessing good stability properties, all suffer the serious disadvantage that they must be used at a relatively high temperature such as 85° C. or higher to be optimally effective in the absence of costly activators. A trend toward lower washing temperatures renders them unacceptable for use in many household washing machines which are now being operated at water temperatures less than about 60° C. In general, effectiveness at lower temperatures would be advantageous because of reduced energy costs, reduced fabric damage or shrinkage, reduced need for sorting out temperature sensitive articles, etc.

To overcome the unsatisfactory low temperature performance of inorganic oxygen releasing compounds, it has been proposed that they be used in combination with so called bleach activators. Generally, these bleach activators are compounds which react with an inorganic oxygen bleach during the bleaching operation to release, in situ, a more reactive oxygen bleach such as a peroxycarboxylic acid. Several serious disadvantages are involved in the use of such combinations of inorganic oxygen bleaches with bleach activators. For example, in typical practice it is necessary to employ a large excess of either the inorganic oxygen releasing compound or the activator in order to obtain an acceptably complete and rapid release of the effective bleaching species. Another disadvantage is that the bleach activator must contain within its structure moieties which, upon release of the effective bleaching species, become side products. These side products contribute little or nothing to bleaching. Thus, the inclusion of these moieties tends to be wasteful.

All of the above-mentioned disadvantages of chlorine bleaches and inorganic oxygen bleaches used alone or in combination with activators can be overcome by the use of effective organic oxygen bleaches, particularly by the use of peroxycarboxylic acids. A number of such peroxycarboxylic acid bleaches are known in the art. However, these prior art peroxycarboxylic acids also exhibit some significant disadvantages. For example, due to their relatively high reactivity, these compounds tend to be difficult to maintain in an undegraded form during storage of products containing them, prior to their use. In some cases, it is impossible to achieve an acceptable shelf life. In other cases, it is necessary to use expensive stabilization systems which may consume large amounts of stabilizing materials. For example, if prior art peroxycarboxylic acid bleaches are incorporated into a complete detergent formulation, stabilization is possible only at substantial extra cost as by encapsulation or other means of ingredient segregation. Examples of prior art teaching the coating technique to isolate peroxycarboxylic acids are U.S. Pat. Nos. 3,847,830 to Williams et al, 4,094,808 to Stewart et al and 4,321,301 to Brichard et al.

Other consequences of inherent molecular instability of peroxycarboxylic acids include the need to blend them with components capable of absorbing energy during their decomposition in order to prevent violent decomposition. See for example U.S. Pat. No. 4,100,095 to Hutchins et al. A further disadvantage of some prior art peroxycarboxylic acids is a lack of selectivity in their bleaching action. Thus, in such cases, dyes on some colored articles are significantly damaged during bleaching, although usually not to as great an extent as with chlorine bleaches.

Because of the above disadvantages there is a continuing need for new peroxycarboxylic acid compounds, effective in bleaching, which overcome or reduce the disadvantages recited above for prior art compounds of this class.

SUMMARY OF THE INVENTION

There has now been discovered a new class of peroxycarboxylic acids generally described as sulfone peroxycarboxylic acids. The class described herein has been found to be more storage stable and less prone toward dye damage than similar prior art peroxycarboxylic acids. Particularly surprising is that some members of the class exhibit a combination of a high level of activity for bleaching or stain removal, a high degree of storage stability, and a very low level of damage to dyes in colored articles subjected to bleaching. Other advantages of many sulfone peroxycarboxylic acids include means of their preparation which are unusually efficient, employment of low cost raw materials in their production, and physical properties which are favorable for efficiently incorporating them in various formulated products.

Sulfone peroxycarboxylic acids in accordance with this invention are represented by the following formula:

wherein A and B are peroxycarboxylic acid compatible organic moieties, bonded to the sulfur atom by a carbon atom at least one of A and B containing at least one

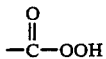

group bonded to a carbon atom except that when A is

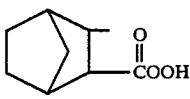

B is not phenyl and when A is

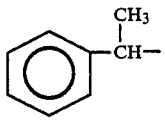

B is not

While not bound by any theory, it appears that the presence of the sulfone group in the sulfone peroxycarboxylic acids has been found to have the effect of stabilizing the compound such that long storage periods are now possible without the traditionally expected large loss in active-oxygen.

Although Formula I above indicates only one sulfone group it is obvious that there are contemplated within the scope of this invention compounds wherein organic moieties A and B may optionally contain one or more additional sulfone groups.

As employed herein "peroxycarboxylic acid compatible" means that the moiety or any substituent group thereon does not react with the peroxycarboxylic acid group under normal conditions of storage and use of the claimed bleaches.

The theoretical active oxygen content of the preferred compounds of this invention will be above about 5.42 percent. Also particularly preferred compounds will contain a total of two peroxycarboxylic acid groups, such groups being bonded directly to separate aromatic rings. Also preferred compounds are those wherein one of A and B is a peroxybenzoic acid group and the other is an alkyl radical whether branched or straight chain, containing from 1 to 10 carbon atoms and more preferably 1 carbon atom.

DETAILED DESCRIPTION OF THE INVENTION

Any number of suitable organic moieties can be employed to provide the intermediate link between the peroxyacid group and the sulfone group. For example, organic moieties may be employed to modify the solubility of the compound at point of use.

Each of the organic moieties may contain one or more peroxycarboxylic groups. Alternatively, effective, stable bleaches are provided by compounds of the present invention wherein only one of the organic moieties contains a peroxyacid group. In fact, organic moieties A and B in the above formula may be the same or different. Embodiments of this invention wherein there are contained from 1 to 4 peroxycarboxylic acid groups are preferred and still more preferred are embodiments containing 1 or 2 peroxycarboxylic acid groups. Variation of organic moieties A and B allows for tailoring desirable compounds through choice of the organic moiety to lend specific properties to the molecule. In the preferred embodiment the compounds of this invention possess at least some degree of water solubility. The solubility of the compounds of this invention is, of course, modified by pH conditions at point of use such as in detergent baths.

Preferably, organic moieties A and B of the above formula are selected from the group consisting of cyclic, linear or branched alkyl groups containing from about 1 to about 16 carbon atoms (more preferably from about 2 to about 10 carbon atoms), aryl groups, aromatic heterocyclic groups, polyaryl groups consisting of from 2 to about 4 annelated benzenoid rings, and combinations thereof. Also, organic moieties A and B can be substituted with essentially any peroxycarboxylic acid compatible group or groups selected from hydroxy, halogen (chloro, bromo, or fluoro), sulfonate, nitro, carboxylic acid, carboxylate salt or ester, phenyl, $C_{1-5}$ alkoxy (e.g. ethoxy), heteroaryl, sulfone, amine oxide, amide, ester, nitrile and sulfate groups and the like to replace a hydrogen atom attached to the organic moieties A or B. The organic moieties A and B may not contain substituents which would react readily with the active oxygen from the peroxyacid group. Common reactive groups may include iodides, ketones, aldehydes, sulfoxides, sulfides, mercaptans, amines, reactive olefins, etc.

The groups A and B may contain any number of combinations of aromatic rings, alkyl chains, substituted aromatic rings, and substituted alkyl chains provided only that all substituents are stable in the presence of a

group. Preferred substituents are located to provide adequate stability and are selected from the group consisting of chloro, nitro, alkyl, aryl, ester,

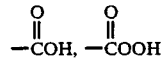

and amide.

A particularly preferred class of peroxy-acids of this invention is represented by the formula

wherein X and Y are peroxycarboxylic acid compatible hydrocarbyl groups, at least one of X and Y being substituted with at least one

group except that when X is

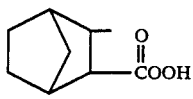

Y is not phenyl and when X is

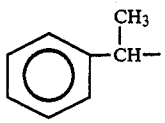

Y is not

Included in this class are compounds of formula II having at least one of X and Y substituted with two peroxycarboxylic acid groups. Such substitution permits greater active oxygen to be generated per unit molecular weight.

Another novel class of sulfone peroxycarboxylic acids of this invention comprises compounds wherein taken together the organic moieties X and Y form a heterocyclic ring wherein the sulfur atom is the hetero atom. Compounds of this type are represented by the formula

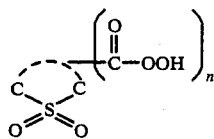

wherein the heterocyclic ring contains at least 4 carbon atoms and n is an integer from 1 to 4, preferably 1 or 2. The peroxycarboxylic acid groups are bonded to carbon atoms. Preferably, the heterocyclic ring contains a total of 4 to 6 carbon atoms although larger heterocyclic rings are contemplated, i.e., as large as 12 carbon atoms.

Included among the hydrocarbyl moieties X and Y of formula II are alkyl, aralkyl inclusive of cyclic, straight and branched chain radicals, such as methyl, ethyl, isopropyl, cyclopropyl, cyclohexyl, tertiary butyl, n-butyl and the various forms of amyl, hexyl, heptyl, octyl, nonyl, decyl, undecyl, dodecyl, tridecyl, tetra- decyl, pentadecyl, hexadecyl, heptadecyl, octadecyl, benzyl, phenylethyl, naphthylethyl, tolylethyl, methylbenzyl, phenylbenzyl and the like, aryl groups and alkaryl groups such as phenyl, biphenyl, tolyl, xylyl, naphthyl, and the like. It is preferred that such X and Y groups contain from 1 to 18 carbon atoms.

The novel sulfone peroxycarboxylic acids of this invention are prepared from the corresponding carboxylic acids, esters, anhydrides, etc. in conventional manner. In a typical procedure the sulfone precursor is reacted with hydrogen peroxide in an acidic medium such as sulfuric acid or methanesulfonic acid. Isolation of the sulfone peroxycarboxylic acid is performed in the usual manner for recovering solids since most of the novel sulfone peroxycarboxylic acids of this invention are normally solid at room temperature.

The desired sulfone carboxylic acid precursors may be formed by oxidation of a corresponding sulfide. This procedure is well known in the art to be performed with common oxidizing agents such as hydrogen peroxide, oxygen, potassium permanganate, etc.

It is recommended that sulfone carboxylic acid precursors which are not sufficiently soluble in the acidic medium during peroxidation be converted to the ester form using low molecular weight alkyl alcohols such as methyl, ethyl or propyl alcohols. The ester form is often more easily peroxidized to the desired sulfone peroxycarboxylic acid. It has been observed that the sulfone group is relatively stable and withstands vigorous peroxidation procedures.

Other acids useful in the peroxidation reaction include various sulfonic acids and strong acid cation exchange resins. Generally, peroxidation is conducted at temperatures in the range of from about 0° C. to about 75° C. depending upon the reactivity of the precursor and the stability of the precursor and the resulting peroxycarboxylic acid.

Generally, it is preferred to employ a stoichiometric excess of peroxidizing agent and then separate the excess agent after peroxidation. Any suitable peroxidizing agent may be employed. Hydrogen peroxide is preferred.

Mixtures of sulfone peroxycarboxylic acids with each other and/or with the corresponding carboxylic acids or esters are included within the scope of this invention. Such mixtures nearly always result when precursors containing two or more groups convertible to peroxycarboxylic acid groups (such as —COOH,—COOR where R is lower alkyl and the like) are reacted with hydrogen peroxide to produce a peroxycarboxylic acid composition. In such mixtures, it is preferred that a substantial fraction such as 50% or more of the resulting molecules have all such groups converted to the peroxy acid group in order to make efficient use of the precursor.

The water solubility of the sulfone peroxycarboxylic acids of this invention can be varied in one or more ways known to one skilled in the art. For example, inclusion of a long alkyl chain tends to depress the water solubility, especially as the number of carbon atoms increases. Also in many cases solubility tends to decrease as molecular weight increases. In any given series of compounds varying primarily in water solubility an optimum degree of water solubility will exist and this can be determined by routine experimentation. In most cases, a relatively low water solubility, i.e. less than about 1% by weight, is preferred because this facilitates efficient separation of the product from excess $H_2O_2$ and acid catalysts used during preparation.

Compounds of this invention can be employed in a variety of modes. Not only can they be employed in dry bleach formulations but also they can be employed in hard surface cleaners, laundry detergents, and machine dishwashing compositions as well as a wide variety of other compositions useful for laundry or other purposes.

The laundry detergent compositions of this invention comprise from about 2 percent to about 80 percent of a detergent surfactant, detergent builder or mixtures thereof and from about 0.1 percent to about 50 percent of the novel sulfone peroxycarboxylic acids of this invention.

Preferably the compositions contain from about 5 percent to about 30 percent detergent surfactant, from about 0 percent to about 50 percent detergent builder and from about 0.5 percent to about 20 percent of the sulfone peroxycarboxylic acids of this invention to give from about 0.05 percent to about 3 percent available oxygen.

Suitable detergent compositions and detergent ingredients are disclosed in U.S. Pat. Nos. 4,166,039, 4,157,978, 4,056,481, 4,049,586, 4,035,257, 4,019,998, 4,000,080, and 3,983,078 all of which are incorporated herein by reference. Disclosures of additional ingredients appear in U.S. Pat. Nos. 4,089,945, 3,987,161 and 3,962,418 incorporated herein by reference. Preferably, the compositions are in solid granular or particulate form and preferably are formulated to prevent reaction of other ingredients with the active oxygen in the novel sulfone peroxycarboxylic acids of this invention.

The dry bleach compositions of this invention comprise from about 0 percent to about 50 percent detergent surfactant, detergent builder or mixtures thereof and from about 1 percent to about 50 percent of the stable sulfone peroxycarboxylic acids of this invention. Preferably the compositions contain from about 5 percent to about 30 percent detergent surfactant, from about 0 percent to about 50 percent detergent builder and from about 0.5 percent to about 25 percent of the sulfone peroxycarboxylic acids of this invention to give about 0.05 percent to about 3 percent active oxygen.

In the following examples, which illustrate the invention, and throughout the specification, parts and percent are by weight unless otherwise indicated.

EXAMPLE 1

Preparation of 3,3'-sulfonyldipropionic acid (precursor).

To a 5000 mL 4 neck glass reaction flask, equipped with a mechanical stirrer, alcohol thermometer, dropping funnel, water cooled condenser, and ice bath were charged 416 g of 3,3'-thiodipropionic acid (Aldrich, 99%) and 2234 mL of glacial acetic acid. The resulting slurry was mixed until uniform and adjusted to 25° C. To the dropping funnel was charged 301.5 mL of 30% aqueous $H_2O_2$. With agitation, the $H_2O_2$ was added over a period of 40 minutes with ice cooling to maintain the temperature in the range of 29°-32° C. Agitation was continued for another 11 minutes. The resulting homogeneous solution was cooled to 24° C., and all but a small reactor heel was transferred to a 4000 mL beaker. To the mixture in the beaker 301.5 mL of 30% $H_2O_2$ was added rapidly with agitation (no temperature rise observed). The heel in the reactor was heated to reflux (alcohol thermometer replaced with a plug at 50° C.), and the mixture in the beaker was added to it via the dropping funnel over a period of 39 minutes (transfer completed by rinsing with 100 mL glacial acetic acid). Refluxing was continued for another 62 minutes, and the resulting white slurry was cooled to 25° C. Excess $H_2O_2$ was destroyed by addition of 500 mL of 5% aqueous $Na_2SO_3$ solution (absence of active oxygen confirmed with starch-iodide test paper), with cooling to maintain 25° C. The solids were collected by filtration, reslurried in 600 mL water, again collected by filtration, washed on the filter with four 400 mL portions of water, and dried at ambient temperature to constant weight. The product weighed 464.00 g, equivalent to a yield of 94.6% of theory based upon the amount of 3,3'-thiodipropionic acid used. Analysis by NMR in DMSO-D6 confirmed that the product was 3,3'-sulfonyldipropionic acid, free of detectable amounts of impurities or retained water.

EXAMPLE 2

Preparation of 3-(cyclohexylsulfonyl)propionic acid (a precursor).

To a 1000 mL 4 neck glass reaction flask equipped with a mechanical stirrer, dropping funnel, thermometer, water cooled condenser, and ice bath were charged 100.18 g of cyclohexylmercaptan and 1 mL of 40% aqueous benzyltrimethylammonium hydroxide solution (as catalyst). To the dropping funnel was charged 84.15 mL (10% excess) of methyl acrylate. With agitation and ice cooling the methyl acrylate was added over a period of 14 minutes at 28°-38° C. Following the addition, the ice bath was replaced by a heating mantle, and agitation was continued at 30±1° C. for 69 minutes. 171.1 mL of 20% aqueous NaOH was charged to the dropping funnel, and 278 mL of absolute ethanol was charged to the reactor. The NaOH (10% excess over methyl acrylate) was added over a period of 9 minutes, the temperature rising to 46.5° C. The mixture was heated to reflux (80° C.) and refluxed for 46 minutes. The mixture was cooled to 25° C. and transferred (with $H_2O$ rinse) to a rotary evaporator. Using aspirator vacuum and a bath temperature of 50°-55° C., 280 mL of volatile material (mostly ethanol) was stripped off and discarded. The residue was a homogeneous, water white solution weighing 360.3 g. The residue was cooled in an ice bath, transferred to a 1000 mL separatory funnel, and reacted therein with 95.8 mL of cold 37% aqueous HCl (10% excess over NaOH). Enough dry NaCl was added in several portions to nearly saturate the aqueous phase. After cooling, shaking, and settling for 30 minutes, the mixture consisted of an upper oil phase containing the bulk of the product and a lower aqueous phase which was drained off and discarded. The oil phase was washed once with an equal volume of nearly saturated aqueous NaCl, and after settling overnight, the wash layer was drained off and discarded. The oil phase was transferred to a 2000 mL 4 neck glass reaction flask, fitted with a dropping funnel, mechanical agitator, alcohol thermometer, reflux condenser, and an ice bath. 860 mL of glacial acetic acid was also charged, part of it being used to rinse residues from the separatory funnel into the reactor. To the dropping funnel was charged 133.3 mL of 30% $H_2O_2$ (50% excess over theoretical for conversion to the sulfoxide). The $H_2O_2$ was added with agitation over a period of 22 minutes with cooling as needed to maintain ≦32° C. Following the addition, agitation was continued without cooling for 68 minutes, the temperature declining to 25.5° C. Leaving a small heel in the reactor, most of the reaction mixture was transferred to a 4000 mL beaker and mixed with another 133.3 mL of 30% $H_2O_2$ (no temperature rise observed). The heel was heated to reflux, and the mixture from the beaker was added to the reactor via the dropping funnel over a period of 37 minutes. Refluxing was continued for another 60 minutes, and the mixture was then cooled to room temperature. Another 102 mL of 30% $H_2O_2$ was added and mixed in, and the mixture was allowed to stand for 4½ days at ambient temperature. Excess $H_2O_2$ was destroyed by mixing with 900 mL water and 219.18 g $Na_2SO_3$ in a 4000 mL beaker at $\leq 50°$ C. The liquid phase was separated from undissolved salts by a combination of decantation and filtration and transferred to a rotary evaporator (in several batches) where volatiles were stripped off at a bath temperature of 51°–52° C. (aspirator vacuum) and discarded. The residue, a thin sludge, became a solid crystalline mass upon cooling and standing. The total product was collected in a 4000 mL beaker and diluted with water to 1000 mL. This mixture was heated to 80° C., at which temperature it was a homogeneous solution. It was then cooled to 18° C., at which temperature it crystallized rapidly to form a thick white slurry. The solids were collected by filtration at 15°–20° C., washed on the filter with water, and dried at ambient temperature to constant weight. The product weighed 129.12 g, equivalent to a yield of 68% of theory based upon the amount of cyclohexylmercaptan used. Analysis by NMR in DMSO-D6 confirmed that the product was 3-(cyclohexylsulfonyl)propionic acid, free of detectable amounts of impurities or retained water.

EXAMPLE 3

Preparation of 4,4'-sulfonyldiperoxybenzoic acid.

The starting material was sulfonyldimethylbenzoate, ground to a powder using a mortar and pestle prior to weighing. To a 400 mL beaker, equipped with a support clamp, heating mantle, thermowell and thermocouple, dropping funnel, and glass and teflon mechanical stirrer, were charged 34.4 g (0.103 mole) of the above powder and 100 mL of 99.5% methanesulfonic acid. After a few minutes mixing at ambient temperature, a uniform slurry was obtained. To the dropping funnel was charged 16.8 mL of 90% aqueous $H_2O_2$ (0.618 mole, 3 fold excess). The slurry in the beaker was heated to 57° C., and the $H_2O_2$ was added dropwise over a period of 37 minutes with agitation. The temperature rose to the range 58°–60° C. and was then maintained there throughout the addition by adjustment, of heat input. Following the addition, agitation was continued for 183 minutes at 58°–62° C. The mixture remained a white slurry throughout the reaction. The mixture was then cooled to 10° C. and filtered. The solids were redispersed in 300 mL of cold (5° 10° C.) pH 5 phosphate buffer solution (prepared by titration of 10% aqueous NaOH to pH 5.0 with 85% $H_3PO_4$). The solids were again collected by filtration and redispersed into 100 mL of cold (5°–10° C.) water. The solids were again collected by filtration and redispersed with 26.1 g powdered boric acid (99.78% $H_3BO_3$) and 100 mL cold (5°–10° C.) 1.96% aqueous boric acid solution. The solids were collected by filtration and dried on a sheet of glass at ambient temperature to constant weight. The dried product weighed 56.32 g. Active oxygen content was determined twice (iodometric titration) obtaining results of 3.71% and 3.73%. The active yield was 63.64% of theory (for complete conversion to the diperacid), calculated as follows:

$$\text{active yield} = \frac{\text{product activity}}{\text{activity of 100\% diperacid}} \times \frac{\text{product weight}}{\text{theoretical weight of diperacid}} \times 100$$

$$= \frac{3.72}{9.46} \times \frac{56.32}{34.80} \times 100 = 63.64\%$$

It is estimated that the product contained about 46.34% boric acid, based upon the amount of powdered boric acid charged. Thus, the activity of the organic fraction was about 3.72/0.5366=6.933%, which is 73.29% of the theoretical 9.46% for the pure diperacid. This activity is equal to that of a mixture consisting of 43.8% 4,4'-sulfonyldiperoxybenzoic acid and 56.2% 4,4'-sulfonylmonobenzoic monoperoxybenzoic acid.

Throughout the above procedure, the only equipment contacting the reaction mixture or product consisted of porcelain, Teflon ®, glass, or polyethylene. Filtrations employed vacuum and used glass microfibre filter media.

EXAMPLE 4

Preparation of 3-(cyclohexylsulfonyl)peroxypropionic acid.

To a 150 mL beaker equipped with a support clamp, ice bath, alcohol thermometer, mechanical stirrer, and dropping funnel were charged 22.03 g (0.1 mole) of powdered 3-(cyclohexylsulfonyl)propionic acid and 29.8 mL of 82 wt. % aqueous $H_2SO_4$. After a few minutes mixing at ambient temperature, a uniform slurry was obtained. To the dropping funnel was charged a solution prepared by adding 33.3 mL of 95.5% $H_2SO_4$ to 17.0 mL of 50% $H_2O_2$ (0.3 mole, 3 fold excess) with stirring and cooling to maintain $\leq 30°$ C., with final cooling to 25° C. With agitation, the mixture in the dropping funnel was added to the beaker over a 10 minute period, the temperature rising to 27° C. The ice bath was not applied because the heat evolution was so small. The mixture was agitated for another 130 minutes, the temperature gradually declining to 26.5° C. Most of the solids dissolved. The mixture was then contacted with ten 25–30 mL portions of methylene chloride at ambient temperature in an effort to recover the product by direct extraction into the methylene chloride. The combined extracts were washed with pH 5 phosphate buffer solution, then washed with water, partially evaporated, mixed with a weighed amount of boric acid, and dried. The weight and active oxygen analysis of this product showed that only 3.57 g of the organic product had been recovered by extraction (~15% of theory) and that its activity was 91.1% of that for the pure peracid. The crude reaction product remaining after methylene chloride extraction was mixed with 100 mL of cold pH 5 buffer with agitation and ice cooling, resulting in immediate formation of a large amount of white solids. The slurry was filtered at 15°–20° C. and the solids were washed on the filter with two 100 mL portions of cold buffer followed by 100 mL cold water. The resulting product was mixed with boric acid and dried and then blended uniformly with most of the product recovered by extraction. The resulting final product weighed about 30 g and had an active oxygen content of 3.27% (boric acid content roughly 47%). The calculated active yield was 61% of theory. (Equipment, analysis, and yield calculation were as described in Example 3.)

EXAMPLE 5

Preparation of 3,3'-sulfonyldiperoxypropionic acid.

A stirred mixture of 100 g of 3,3'-sulfonylbispropionic acid and 600 mL of methanesulfonic acid (99.5% purity from Alfa) in a one liter beaker was heated to 35° C. in a heated water bath. Heating was then stopped and 107 g of 90% hydrogen peroxide was then added dropwise via a pipette over approximately one hour. During the addition of the hydrogen peroxide, the temperature of the reaction mixture rose to a temperature ranging between 40° C. and 45° C. After the addition of the hydrogen peroxide was completed, the stirred reaction mixture was kept at approximately 40° C. for two hours. Throughout this procedure the reaction mixture had two phases, a solid phase and a liquid phase. Heating was stopped and the reaction mixture was cooled to approximately 10° C. in an ice bath. The solid-liquid mixture was then poured onto ice prepared from deionized water. The solid was filtered from solution using a coarse sintered-glass funnel. The solid was then washed four times with cold, deionized water. For each of the washings the solid was transferred from the funnel to a beaker, was slurried with approximately 500-600 mL of cold deionized water and was filtered away from the solution using the coarse sintered-glass funnel. The solid was transferred to a watchglass and dried overnight. The dried product weighed 95.1 g which is a yield of 82.5% of theoretical based upon the weight of starting sulfone carboxylic acid. On the basis of an average of two titrations the product contained 13.12% available oxygen representing 99.3% of the theoretical value.

Stabilization with Boric Acid

The product was mixed with an equal weight of boric acid powder. This mixture was put through a #30 polyethylene sieve. Particle size would be <600 microns. The mixture was then bottled and the bottle was shaken to blend well the boric acid with the product.

Percent active oxygen in the boric acidstabilized product was found to be 6.68%.

EXAMPLE 6

Preparation of 4-(methylsulfonyl)benzoic acid (a precursor)

A mixture of 5 g of 4-(methylthio)-benzoic acid (97%) and 30 mL of glacial acetic acid was formed. The mixture was cooled in a water bath containing a small amount of ice. To the mixture was added 8.5 g of 30hydrogen peroxide gradually over one hour. No temperature rise was observed during the addition of the hydrogen peroxide. The reaction mixture was then heated for one and a half hours with the temperature ranging between 70° C. and 100° C. Heating was stopped and the reaction mixture was allowed to cool to room temperature. A solid was present in the reaction mixture. A solution of 3 g of sodium sulfite in 57 g of water was added to the reaction mixture. The solid was filtered from solution and was washed three times with cold deionized water. The solid was transferred to a watchglass and dried overnight. The dried product weighed 5.25 g which is a yield of 88.1% of the theoretical based upon the amount of the starting benzoic acid.

An NMR spectrum of the product in deuterated dimethylsulfoxide was in agreement with a literature spectrum of the compound in the same solvent ("Aldrich Library of NMR Spectra").

This batch of product was combined with the product from a larger scale batch (4x). The combined products were recrystallized from ethanol. The recrystallized material was used in the synthesis of 4-(methylsulfonyl)peroxybenzoic acid.

EXAMPLE 7

Preparation of 4-(methylsulfonyl)peroxybenzoic acid.

A stirred mixture of 5 g of 4-(methylsulfonyl)benzoic acid and 50 mL of methanesulfonic acid froze when it was cooled in an ice bath. The ice bath was removed and when the mixture was partially melted, stirring was resumed and the addition of 2.83 g of 90% hydrogen peroxide was started. The 90% hydrogen peroxide was added gradually over ten minutes. When the addition of the hydrogen peroxide was completed, the reaction mixture was still partially frozen. A water bath of cold tap water was used to warm the reaction mixture. The temperature of the reaction mixture rose briefly to 28° C. One hour after the addition of the hydrogen peroxide was started, the reaction mixture was heated for 70 minutes within a temperature range of 40° C.–45° C. The stirred reaction mixture was then cooled in an ice bath. A solid precipitated from solution. When the temperature of the reaction mixture was between 10° C.–15° C., the solid product was filtered from solution. A second fraction of solid product was collected when the filtrate was poured onto ice prepared from deionized water and the solid which formed was filtered away from solution. Fraction one was washed four times with 60 mL each time of cold deionized water. Fraction two was washed four times with 150 mL each time of cold deionized water. Both fractions of the solid product were very easy to wash and to isolate by filtration. The two fractions were each transferred to a watchglass and dried overnight. The dried solids were fine, dry powders.

|  | Fraction 1 | Fraction 2 |
| --- | --- | --- |
| Weight of product: (The combined weights would represent a yield of 81.8% of the theoretical 5.4 g). | 3.3331 g | 1.0836 g |
| Percent by weight of active oxygen: | 6.67 | 6.54 |
| Percent of theoretical active oxygen: | 90.1 | 88.4 |
| Melting point: | 154.5–156° C. | |

Stabilization with boric acid

The two fractions were combined and an equal weight of boric acid powder was added. The mixture was put through a #30 polyethylene sieve. Particle size would be <600 microns. The mixture was then bottled and the bottle was shaken to blend well the boric acid with the product.

Percent by weight of active oxygen in the boric acidstabilized product was 3.31%.

EXAMPLE 8

Preparation of 11-mercaptoundecanoic acid (a precursor).

A mixture of 200 g of 11-bromoundecanoic acid, 60 g of thiourea and 600 mL of absolute ethanol was stirred and heated at reflux for two hours. After heating was stopped a solution of 80 g of sodium hydroxide in 250 mL of water was then added dropwise. The mixture was held overnight and then heated at reflux for three hours. After cooling to room temperature a solid precipitated from solution. The reaction mixture was poured into a mixture of ice and 200 g of concentrated hydrochloric acid. The solids were filtered from solution then slurried with ice water, isolated by filtration and washed twice. The off-white solid was stored in a crystallizing dish for one week, then dried under vacuum (~1 mm of Hg) at about 45° C. The product was distilled under vacuum (~1 mm of Hg at ~160° C.). NMR analysis indicated the desired product was obtained. The distilled product weighed 74.7 g representing 45.46% yield based upon the weight of starting 11-bromoundecanoic acid.

EXAMPLE 9

Preparation of 11-(methylthio)undecanoic acid (a precursor).

Into a 3-neck round-bottom flask fitted with a condenser and an addition funnel were added 20 g of 11-mercaptoundecanoic acid, 13 g of methyl iodide and 200 mL of ethanol. A slow flow of nitrogen through the reactor was started to exclude oxygen because mercaptans can be converted into disulfides in the presence of air and strong alkali. A solution of 7.33 g of sodium hydroxide in 14.66 g of water was added dropwise to the reaction mixture via the addition funnel. The reaction mixture was kept at room temperature overnight. Any unreacted methyl iodide, the ethanol and the water were removed using a rotovap. The residue was acidified using a mixture of concentrated hydrochloric acid and ice. After isolation the product was distilled. After a small amount of a low boiling fraction was collected, the desired product was collected at ~1 mm of Hg at 180° C. weighing 22.75 g. The crude product was distilled to yield 12.5 g of desired product representing 58.7% of theoretical based upon the weight of starting 11-mercaptoundecanoic acid.

EXAMPLE 10

Preparation of 11-(methylsulfonyl)undecanoic acid (a precursor).

Into a three-neck round-bottom flask fitted with an overhead mechanical stirrer, thermometer and addition funnel were added 12.3 g of 11-(methylthio)undecanoic acid and 53 mL of acetic acid. The mixture was warmed slightly to help all of the solid to dissolve in the acetic acid. At a temperature of approximately 30° C., the dropwise addition of 24 g of 30% hydrogen peroxide was started. After the addition was completed, the reaction mixture was stirred without heating for an hour. The mixture was then heated at slow reflux for an hour. The reaction mixture was cooled first to room temperature and then in an ice bath. Aqueous sodium sulfite (5%) was added to decompose all active oxygen present. The solid was filtered and washed several times with cold deionized water. The solid was then dried overnight on a watchglass. The product weighed about 7.7 g (55% of theoretical) based upon the weight of starting acid.

EXAMPLE 11

Preparation of 11-(methylsulfonyl)peroxyundecanoic acid.

A stirred mixture of 3 g of 11-(methylsulfonyl)undecanoic acid and 30 mL of methanesulfonic acid was heated to approximately 40° C. The solid dissolved only partially in the methanesulfonic acid at this temperature. Then 1.29 g of 90% hydrogen peroxide was added dropwise. The temperature of the reaction mixture was reduced to room temperature after twenty minutes of reaction time. For the remainder of the two hour reaction time, the reaction mixture was not heated and became homogeneous. The reaction mixture was then cooled in an ice bath forming a solid which was then filtered from solution. The filtrate was poured onto ice prepared from distilled water. A solid formed which was filtered from solution. The two solids collected were combined and washed several times with cold deionized water until the filtrate was no longer strongly acidic. The solid was dried overnight on a watchglass, weighed 2.91 g and had 4.8% by weight active oxygen (84.1% of theoretical).

EXAMPLE 12

Preparation of 3-(n-decylthio)propionitrile (a precursor).

To a 250 mL round-bottomed flask fitted with an overhead mechanical stirrer, a thermometer and an addition funnel were charged 87 g of 1-decanethiol and 20 drops of a 21% by weight solution of sodium ethoxide in ethanol. The mixture was cooled to 10° C. using an ice bath. Then the dropwise addition of 53 g of acrylonitrile was started. After addition of a portion of the acrylonitrile, 10 drops of 21% by weight solution of sodium ethoxide in ethanol were added. The temperature of the reaction mixture during the addition of the remaining acrylonitrile ranged between 30° C. and 35° C. The reaction mixture was then kept at room temperature overnight (~19 hours). The unreacted acrylonitrile was then removed by distillation at atmospheric pressure. The remaining material was then distilled at ~1 mm pressure. A first fraction was collected from 150° C. to 160° C. Fraction one had a strong odor of thiol. A second and final fraction was collected at 160° C. The second fraction had a faint odor of thiol. An NMR spectrum indicated the second fraction to be the desired product 83.5% of theoretical (94.9 g) based upon the weight of 1-decanethiol employed.

EXAMPLE 13

Preparation of 3-(n-decylsulfonyl)peroxypropionic acid.

The product of Example 12 was converted to the corresponding carboxylic acid by alkaline hydrolysis followed by acidification and then to the corresponding sulfone carboxylic acid by oxidation in accordance with a procedure found in U.S. Pat. No. 3,857,875 to Brady et al. A stirred mixture of 5 g of 3-(n-decylsulfonyl)propionic acid and 50 mL of methanesulfonic acid was heated to 40±3° C. The 3-(n-decylsulfonyl)propionic acid dissolved only partially in the methanesulfonic acid at this temperature. Then 2.04 g of 90% hydrogen peroxide was added dropwise via pipette over ten minutes. Before the addition of the hydrogen peroxide was completed, the reaction mixture became thick from precipitation of a solid. After the addition of the 90% hydrogen peroxide was completed, the heating of the reaction mixture was continued at 40±3° C. until the reaction time totalled ninety minutes beginning at the start of the addition of the hydrogen peroxide. The reaction mixture was then cooled in an ice bath at 10° C. The solid was then filtered from solution using a coarse sintered-glass funnel, then transferred to a beaker containing 200 mL of ice water prepared from deionized water. The product was washed twice with ice water, filtered and dried to provide 4.63 g of the desired product (87.6% of theoretical based upon the weight of starting 3-(n-decylsulfonyl)propionic acid). The product was found to have 5.32% active oxygen. The product was stabilized with an equal weight of boric acid and put through a #30 polyethylene sieve which provided a particle size of less than 600 microns. The stabilized product contained 2.58% by weight active oxygen.

EXAMPLE 14

Preparation of Sulfonyldiperoxyacetic Acid.

A mixture of 16.32 mL of 90% aqueous hydrogen peroxide (0.6 mole), 2.3 mL of deionized water and 18.17 mL of 95.5% sulfuric acid was formed in a 150 mL beaker equipped with an ice bath, alcohol thermometer and mechanical stirrer. The water and sulfuric acid were added sequentially to the $H_2O_2$ with cooling and stirring to hold the temperature of the mixture to about 25° C. This mixture was added to 18.215 g (0.1 mole) of sulfonyldiacetic acid in admixture with 100 mL of methylene chloride without cooling over a period of about 8 minutes with agitation. The resulting combination formed two liquid phases and one solid phase. Agitation of this mixture was continued for three hours with the temperature in the range of 20°-22° C. under cover to reduce loss of methylene chloride. The mixture was then cooled to about 5° C. and diluted with 18 mL of deionized water added gradually with stirring and cooling. The solids were collected, reslurried with methylene chloride and treated with 80 mL of 6% aqueous sodium bicarbonate. The solids were collected and similarly treated with another 40 mL of 6% NaHCOs resulting in a final pH of about 4. The recovered solids appeared reduced by the reslurry operations and were combined with 2.91 g of dry powdered boric acid. The mixed solids were dried to constant weight (5.24 g) and found to have an active oxygen content of 5.03%.

It was estimated that the organic fraction of the product contained at least 55% diperacid, plus a considerable amount of the monoperacid.

EXAMPLE

BLEACHING PERFORMANCE

In all of the tests below a detergent is employed as a control at a use level of 1.5 g/L of wash solution. Various bleach compounds of this invention were added to portions of the detergent composition in the amounts shown below in the tables. Each test series contained a control. The detergent formulation is as follows:

| Ingredient | Weight % |
|---|---|
| Sodium alkyl benzene sulfonate | 16 |
| Sodium carbonate | 10 |
| Sodium silicate (47% solids) | 9 |
| Water | 8 |
| Carboxymethyl cellulose | 1 |
| Sodium sulfate | 24 |

| Ingredient | Weight % |
|---|---|
| Sodium tripolyphosphate | 32 |

All of the examples below were conducted at the same wash conditions of 100° F. and with water having a hardness level of 150 ppm (3:2 mole ratio of calcium to magnesium calculated as calcium carbonate). In each test a set of three swatches were evenly stained. After staining, the light reflectance value ($Rd_i$) was measured using the Gardner XL-23 Tristimulator Colorimeter manufactured by Gardner Laboratory, Inc., Bethesda, Md.

A Terg-o-tometer was employed to test the bleaching performance of the bleach compounds. In each test three stained swatches together with three unstained swatches were placed in a cylindrical container with 1 liter of water and 1.5 g of detergent together with a weighed amount of a bleach compound of this invention. Two minutes were allowed for the detergent to dissolve. The washing operation covered a period of 10 minutes after which the laundered swatches were rinsed with clear water and dried. Light reflectance measurements of each cleaned dried swatch were made and averaged ($Rd_f$). The difference ($\Delta Rd$) of these readings for each type of stain is reported in the tables below. ($\Delta Rd = Rd_f - Rd_i$)

The bleach compounds employed in the following examples are represented by the following structure wherein A and B are defined in the tables below.

The tests in Tables I and II below are separate and each includes a control result. In some instances compounds of this invention employed in the separate tests were prepared at different times and in small amounts. The results of each test are comparable only within the context of the individual tests with control data unless otherwise noted. In Tables I and II below the fabric type and kind of stain are listed at the top of each column of data. The notation of poly/cotton means a fabric blend having a ratio of 50:50 of polyester and cotton.

In addition to $\Delta Rd$ data there is reported in the Tables below the percent soil removal (%SR) which may be related to visual effect. Percent soil removal reported in the Tables below was calculated according to the formula:

$$\frac{\Delta Rd}{100 - Rd_i} \times 100 = \text{percent soil removal}$$

wherein $Rd_i$ is the reflectance data obtained by measuring the reflectance of the test swatches after staining but before bleaching in accordance with the procedure described above.

TABLE I

| A | B | g/L bleach | ppm avail oxygen | poly/cotton coffee | | cotton grass | | cotton wine | |
|---|---|---|---|---|---|---|---|---|---|
| | | | | % SR | ΔRd | % SR | ΔRd | % SR | ΔRd |
| Control | | — | 0 | 18.0 | 8.3 | 41.0 | 15.5 | 19.0 | 10.2 |

TABLE I-continued

| A | B | g/L bleach | ppm avail oxygen | poly/cotton coffee % SR | ΔRd | cotton grass % SR | ΔRd | cotton wine % SR | ΔRd |
|---|---|---|---|---|---|---|---|---|---|
|  | $-(CH_2)_2-\overset{O}{\underset{\|}{C}}-OOH$ | .2516 | 8.00 | 29.0 | 13.4 | 52.5 | 19.5 | 39.7 | 21.7 |
| 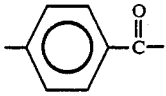 | 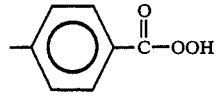 | .2051 | 8.00 | 37.9 | 17.8 | 59.8 | 22.3 | 37.5 | 20.5 |
| $-(CH_2)_2\overset{O}{\underset{\|}{C}}-OOH$ | $-(CH_2)_2\overset{O}{\underset{\|}{C}}-OOH$ | .1207 | 8.00 | 21.5 | 9.7 | 46.4 | 16.9 | 29.0 | 15.7 |
| $-(CH_2)_9CH_3$ | $-(CH_2)_2\overset{O}{\underset{\|}{C}}-OOH$ | .3101 | 8.00 | 44.9 | 20.1 | 71.8 | 26.9 | 34.2 | 18.7 |
| $-CH_3$ | 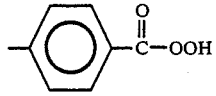 | .2439 | 8.00 | 29.4 | 13.1 | 50.2 | 19.0 | 44.2 | 24.0 |

TABLE II

| A | B | g/L bleach | ppm avail oxygen | cotton wine % SR | ΔRd | cotton clay % SR | ΔRd | cotton grass % SR | ΔRd |
|---|---|---|---|---|---|---|---|---|---|
| Control | | — | 0 | 20.2 | 11.1 | 37.9 | 17.3 | 28.5 | 11.0 |
| $HOO\overset{O}{\underset{\|}{C}}-CH_2-$ | $-CH_2-\overset{O}{\underset{\|}{C}}OOH$ | .1501 | 8.00 | 27.7 | 15.1 | 41.3 | 18.5 | 31.0 | 12.1 |
| $CH_3-$ | $-(CH_2)_{10}\overset{O}{\underset{\|}{C}}-OOH$ | .3150 | 8.00 | 41.1 | 22.4 | 41.1 | 18.5 | 44.6 | 17.4 |
| 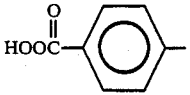 | 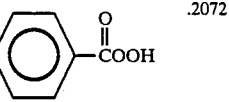 | .2072 | 8.00 | 38.7 | 21.4 | 55.9 | 25.0 | 43.4 | 16.6 |
| Dodecanediperoxoic Acid* | | .1468 | 8.00 | 34.7 | 19.0 | 57.7 | 25.9 | 41.6 | 16.0 |

*known prior art bleach

EXAMPLE 16

STABILITY TESTS

Improved stability of the compounds of this invention are shown by several test procedures described below. In one such test a value "$t_{50}$" is determined which is a measure of the amount of time required for a bleach compound to lose 50% of its originally determined amount of active oxygen. This value is measured for peroxyacids and formulations thereof by incubating the samples in open glass vials at 39° C. and 85% relative humidity. At periodic intervals, aliquot samples are taken and percent active oxygen (%AO) is measured by iodometric titration.

A plot of A/Ao versus time where A=%AO @t=incubation time and A0=%AO@t=0 generates a curve which shows the decomposition of the peracid. Since most organic peracids decompose via an accelerating autocatalytic route, storage stability is reported as "$t_{50}$".

Data for several of the sulfone peroxycarboxylic acids and, for comparison, several prior art peracids are presented below in Table III.

Other determinations were obtained from the above-described test by calculating data from the plot A/Ao to determine the amount of active oxygen in the sample after a period of 30 days. The results are reported in Table III as the percentage of the original amount of active oxygen in the sample.

TABLE III

| | 85% R.H., 39° C. | |
|---|---|---|
| Sample | $t_{50}$ (days) | % $A_o$ Retained at 30 days |
| Magnesium monoperoxyphthalate hexahydrate | 35 | 53 |
| Dodecanediperoxycarboxylic Acid, w/boric acid | 30 | 50 |
| n-Decylbutanediperoxoic Acid, w/boric acid | 5–20 | <50 |
| 1,4-Phenylenediperoxyacetic Acid, w/boric acid | 12.5 | 15 |
| Sulfonyldiperoxypropionic Acid, | 28 | 41 |

TABLE III-continued

| | 85% R.H., 39° C. | |
|---|---|---|
| Sample | t₅₀ (days) | % A₀ Retained at 30 days |
| w/boric acid Sulfonyldiperoxybenzoic Acid, w/boric acid | | 96 |
| 4-Methylsulfonylperoxybenzoic Acid, w/boric acid | | 94 |
| 3-Decylsulfonylperoxypropionic Acid, w/boric acid | | 92 |

In another procedure the temperature of onset of self-heating for bleach compounds and formulations thereof was determined by the following procedure employing accelerating rate calorimetery (ARC). In this procedure samples to be tested are monitored for temperature changes as they are heated in stepped increments of five degrees centigrade. After each step ten minutes is allowed for thermal equilibrium to occur followed by a hold time of twenty minutes at adiabatic conditions. This method continues until the onset of selfheating is observed. The results of this test appear in Table IV under the column marked "A.R.C.". Several known prior art bleaches were included for comparison.

Also shown in Table IV are data obtained in a procedure to determine the percent active oxygen remaining in boric acid stabilized formulations of compounds of this invention. In this procedure 100 g of the formulation is placed in an oven held at 50° C. for 7 days. Open polyethylene containers are employed to hold the formulations. The percent of the initial active oxygen remaining in the formulation after 7 days is reported in Table IV under the column marked "Ambient Humidity, 50° C." indicating that the samples were in contact with ambient atmosphere during the test period.

TABLE IV

| Sample | A.R.C. Onset of Self-heating (°C.) | Ambient Humidity 50° C. % A₀ Retained After 7 Days |
|---|---|---|
| Magnesium monoperoxyphthalate hexahydrate | 78 | — |
| Dodecanediperoxycarboxylic Acid, w/boric acid | 60 | — |
| 1,4-Phenylenediperoxyacetic Acid w/boric acid | 51 | — |
| Sulfonyldiperoxypropionic Acid, w/boric acid | 96 | 85 |
| Sulfonyldiperoxybenzoic Acid, w/boric acid | — | 99 |

In addition to the compounds of this invention described by the above examples, any number of other compounds are contemplated to be within the spirit and scope of this invention. Some examples of such compounds are represented by the formulae below:

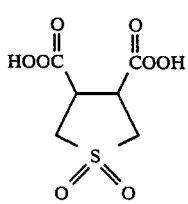

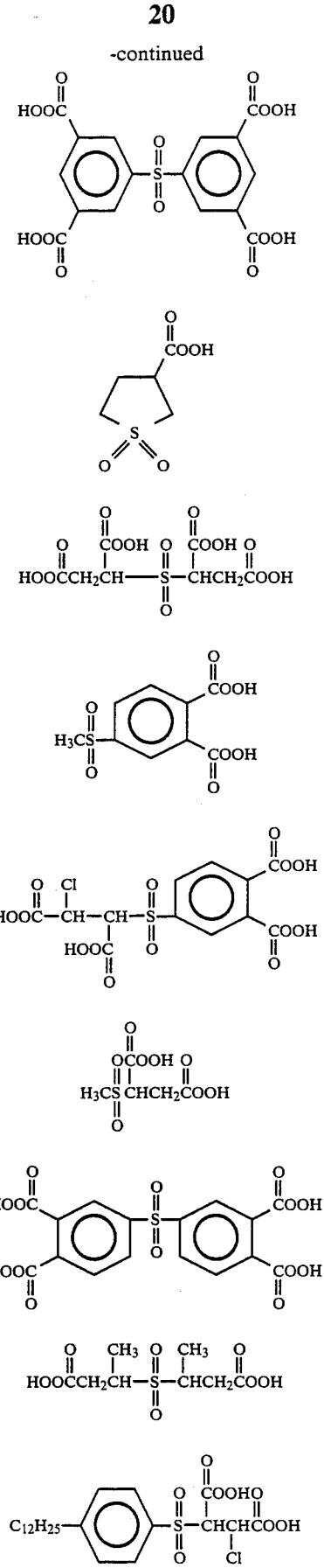

-continued

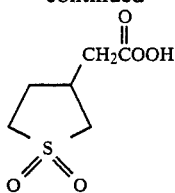

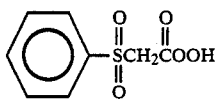

The sulfone peroxycarboxylic acids can be employed alone or be combined with other materials in any number of ways to produce formulated products. Examples of such formulated products include but are not limited to complete laundry detergents, dry bleach formulations, machine dishwashing formulations, bleach releasing articles such as pouches, fabric sheets, and the like, bleaching formulations for use in dry cleaning operations, products for use in textile or paper manufacture, hard surface cleaners, and the like. Among other known ingredients typically employed in such formulations are stabilizers, chelating agents, solubilizers, surfactants, diluents, detergent builders, fragrances, pH adjustment agents, abrasives, optical brighteners, coloring agents, exotherm control agents, solvents, encapsulation agents, enzymes, etc. All such formulations which comprise a bleach effective amount of a sulfone peroxycarboxylic acid are within the scope of this invention. It is obvious that materials selected to provide the above formulations must be compatible with peroxycarboxylic acids of this invention or means must be taken to segregate the material from the bleach.

Typical pH adjustment agents are used to alter or maintain aqueous solutions of the instant compositions during use within the 5 to 10 pH range in which peroxyacid bleaching agents are generally most effective. Depending upon the nature of other optional composition ingredients, pH adjustment agents can be either of the acid or base type. Examples of acidic pH adjustment agents designed to compensate for the presence of other highly alkaline materials include normally solid organic and inorganic acids, acid mixtures and acid salts. Examples of such acidic pH adjustment agents include citric acid, glycolic acid, sulfamic acid, sodium bisulfate, potassium bisulfate, ammonium bisulfate and mixtures of citric acid and lauric acid. Citric acid is preferred by virtue of its low toxicity and hardness sequestering capability.

Optional alkaline pH adjustment agents include the conventional alkaline buffering agents. Examples of such buffering agents include such salts as carbonates, bicarbonates, phosphates, silicates and mixtures thereof.

Since the proxyacid compounds used in the compositions of the present invention are subject to the loss of available oxygen when contacted by heavy metals, it is desirable to include a chelating agent in the compositions. Such agents are preferably present in an amount ranging from about 0.005% to about 1.0% based on the weight of the composition. The chelating agent can be any of the well known agents, but certain are preferred. U.S. Pat. No. 3,442,937, May 6, 1969, to Sennewald et al, discloses a chelating system comprising quinoline or a salt thereof, an alkali metal polyphosphate, and, optionally, a synergistic amount of urea. U.S. Pat. No. 2,838,459, July 10, 1958, to Sprout, Jr., discloses a variety of polyphosphates as stabilizing agents for peroxide baths. These materials are useful herein. U.S. Pat. No. 3,192,255, June 29, 1965, to Cann, discloses the use of quinaldic acid to stabilize percarboxylic acids. This material, as well as picolinic acid and dipicolinic acid, would also be useful in the compositions of the present invention. A preferred chelating system for the present invention is the alkali metal polyphosphate system.

In addition to the above-mentioned chelating systems to tie up heavy metals in the peroxyacid compositions, coating materials (encapsulating agents) may also be used as stabilizers to extend the shelf life of dry granular compositions. Such coating materials may be in general, acids, esters, and hydrocarbons and include such things as wide varieties of fatty acids, derivatives of fatty alcohols such as esters and hydrocarbon oils and waxes. These materials aid in preventing moisture from reaching the peroxyacid compound. Secondly, the coating may be used to segregate the peroxycarboxylic compound from other agents which may be present in the composition and adversely affect the peroxycarboxylic's stability. The amount of the coating material used is generally from about 2.5% to about 15% based on the weight of the peroxycarboxylic acid compound.

It is known to combine peroxycarboxylic acids with exotherm control agents to prevent runaway reaction in the event of overheating, etc. The use of boric acid as an exotherm control agent has been described in U.S. Pat. No. 4,100,095, issued July 11, 1978 to Hutchins et al. Other possible exotherm control agents include hydrates of salts such as magnesium sulfate, calcium sodium sulfate, magnesium nitrate, potassium aluminum sulfate, and aluminum sulfate, and the like as disclosed in U.S. Pat. No. 3,770,816, issued Nov. 6, 1973 to Nielson. Such materials may be employed in conjunction with sulfone peroxycarboxylic acids.

Agents which improve the solubility of the sulfone peroxycarboxylic acid product such as sodium sulfate, starch, cellulose derivatives, surfactants, etc., are also advantageously used herein. These agents can be called solubilizers and are generally used in an amount of from about 10% to about 200% based on the weight of the peroxyacid.

Optional materials for the instant bleaching compositions can include such standard detergent adjuvants as surfactants and builders. Optional surfactants are selected from the group consisting of organic anionic, nonionic, ampholytic, and zwitterionic surfactants and mixtures thereof. Optional builder materials include any of the conventional organic and inorganic builder salts including carbonates, silicates, acetates, polycarboxylates and phosphates If the instant stabilized bleaching compositions are employed as part of a conventional fabric laundering detergent composition, the instant bleaching system generally comprises from about 1% to about 40% by weight of such conventional detergent compositions. Conversely, the instant bleaching compositions can optionally contain from about 60% to about 99% by weight of conventional surfactant and builder materials. Further examples of suitable surfactants and builders are given below.

Water-soluble salts of the higher fatty acids, i.e., "soaps", are useful as the anionic surfactant herein. This class of surfactants includes ordinary alkali metal soaps such as the sodium, potassium, ammonium and alkanolammonium salts of higher fatty acids containing from about 8 to about 24 carbon atoms and preferably from about 10 to about 20 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soaps.

Another class of anionic surfactants includes water-soluble salts, particularly the alkali metal, ammonium and alkanolammonium salts, of organic sulfuric reaction products having in their molecular structure an alkyl group containing from about 8 to about 22 carbon atoms and a sulfonic acid or sulfuric acid ester group. (Included in the term "alkyl" is the alkyl portion of acyl groups.) Examples of this group of synthetic surfactants which can be used in the present detergent compositions are the sodium and potassium alkyl sulfates, especially those obtained by sulfating the higher alcohols ($C_8$–$C_{18}$ carbon atoms) produced by reducing the glycerides of tallow or coconut oil; and sodium and potassium alkyl benzene sulfonates, in which the alkyl group contains from about 9 to about 15 carbon atoms in straight chain or branched chain configuration, e.g., those of the type described in U.S. Pat. Nos. 2,220,099, and 2,477,383, incorporated herein by reference.

Other anionic surfactant compounds useful herein include the sodium alkyl glyceryl ether sulfonates, especially those ethers or higher alcohols derived from tallow and coconut oil; sodium coconut oil fatty acid monoglyceride sulfonates and sulfates; and sodium or potassium salts of alkyl phenol ethylene oxide ether sulfate containing about 1 to about 10 units of ethylene oxide per molecule and wherein the alkyl groups contain about 8 to about 12 carbon atoms.

Other useful anionic surfactants herein include the water-soluble salts of esters of α-sulfonated fatty acids containing from about 6 to 20 carbon atoms in the ester group; water-soluble salts of 2-acyloxy-alkane-1-sulfonic acids containing from about 2 to 9 carbon atoms in the acyl group and from about 9 to about 23 carbon atoms in the alkane moiety; alkyl ether sulfates containing from about 10 to 20 carbon atoms in the alkyl group and from about 1 to 30 moles of ethylene oxide; water-soluble salts of olefin sulfonates containing from about 12 to 24 carbon atoms; and β-alkyloxy alkane sulfonates containing from about 1 to 3 carbon atoms in the alkyl group and from about 8 to 20 carbon atoms in the alkane moiety.

Preferred water-soluble anionic organic surfactants herein include linear alkyl benzene sulfonates containing from about 11 to 14 carbon atoms in the alkyl group; the tallow range alkyl sulfates; the coconut range alkyl glyceryl sulfonates; and alkyl ether sulfates wherein the alkyl moiety contains from about 14 to 18 carbon atoms and wherein the average degree of ethoxylation varies between 1 and 6.

Specific preferred anionic surfactants for use herein include: sodium linear $C_{10}$–$C_{12}$ alkyl benzene sulfonate; triethanolamine $C_{10}$–$C_{12}$ alkyl benzene sulfonate; sodium tallow alkyl sulfate; sodium coconut alkyl glyceryl ether sulfonate; and the sodium salt of a sulfated condensation product of tallow alcohol with from about 3 to about 10 moles of ethylene oxide.

It is to be recognized that any of the foregoing anionic surfactants can be used separately herein or as mixtures.

Nonionic surfactants include the watersoluble ethoxylates of $C_{10}$–$C_{20}$ aliphatic alcohols and $C_6$–$C_{12}$ alkyl phenols. Many nonionic surfactants are especially suitable for use as suds controlling agents in combination with anionic surfactants of the type disclosed herein.

Semi-polar surfactants useful herein include water-soluble amine oxides containing one alkyl moiety of from about 10 to 28 carbon atoms and 2 moieties selected from the group consisting of alkyl groups and hydroxyalkyl groups containing from 1 to about 3 carbon atoms; watersoluble phosphine oxides containing one alkyl moiety of about 10 to 28 carbon atoms and 2 moieties selected from the group consisting of alkyl groups and hydroxyalkyl groups containing from about 1 to 3 carbon atoms; and water-soluble sulfoxides containing one alkyl moiety of from about 10 to 28 carbon atoms and a moiety selected from the group consisting of alkyl and hydroxyalkyl moieties of from 1 to 3 carbon atoms.

Ampholytic surfactants include derivatives of aliphatic or aliphatic derivatives of heterocyclic secondary and tertiary amines in which the aliphatic moiety can be straight chain or branched and wherein one of the aliphatic substituents contains from about 8 to 18 carbon atoms and at least one aliphatic substituent contains an anionic water-solubilizing group.

Zwitterionic surfactants include derivatives of aliphatic quaternary ammonium, phosphonium and sulfonium compounds in which the aliphatic moieties can be straight or branched chain, and wherein one of the aliphatic substituents contains from about 8 to 18 carbon atoms and one contains an anionic watersolubilizing group.

The instant granular compositions can also comprise those detergency builders commonly taught for use in laundry compositions. Useful builders herein include any of the conventional inorganic and organic water-soluble builder salts, as well as various water-insoluble and socalled "seeded" builders.

Inorganic detergency builders useful herein include, for example, water-soluble salts of phosphates, pyrophosphates, orthophosphates, polyphosphates, phosphonates, carbonates, bicarbonates, borates and silicates. Specific examples of inorganic phosphate builders include sodium and potassium tripolyphosphates, pyrophosphates, and hexametaphosphates. The polyphosphonates specifically include, for example, the sodium and potassium salts of ethane 1-hydroxy-1, 1-diphosphonic acid, and the sodium and potassium salts of ethane-1,1,2-triphosphonic acid. Examples of these and other phosphorus builder compounds are disclosed in U.S. Pat. Nos. 3,159,581; 3,213,030; 3,422,021; 3,422,137; 3,400,176 and 3,400,148; incorporated herein by reference. Sodium tripolyphosphate is an especially preferred, water-soluble inorganic builder herein.

Non-phosphorus containing sequestrants can also be selected for use herein as detergency builders. Specific examples of non-phosphorus, inorganic builder ingredients include water-soluble inorganic carbonate, bicarbonate, borate and silicate salts.

Water-soluble, organic builders are also useful herein. For example, the alkali metal, ammonium and substituted ammonium polyacetates, polyacetal carboxylates, carboxylates, polycarboxylates, succinates, and polyhydroxysulfonates are useful builders in the present compositions and processes. Specific examples of the polyacetate and polycarboxylate builder salts include sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Highly preferred non-phosphorous builder materials (both organic and inorganic) herein include sodium carbonate, sodium bicarbonate, sodium silicate, sodium citrate, sodium oxydisuccinate, sodium mellitate, sodium nitrilotriacetate, and sodium ethylenediaminetetraacetate, and mixtures thereof.

Another type of detergency builder material useful in the present compositions and processes comprises a water-soluble material capable of forming a water-insoluble reaction product with water hardness cations in combination with a crystallization seed which is capable of providing growth sites for said reaction product.

Specific examples of materials capable of forming the water-insoluble reaction product include the water-soluble salts of carbonates, bicarbonates, sesquicarbonates, silicates, aluminates and oxalates. The alkali metal, especially sodium, salts of the foregoing materials are preferred for convenience and economy.

Another type of builder useful herein includes various substantially water-insoluble materials which are capable of reducing the hardness content of laundering liquors, e.g., by ion-exchange processes. Examples of such builder materials include the phosphorylated cloths disclosed in U.S. Pat. No. 3,424,545, Bauman, issued Jan. 28, 1969, incorporated herein by reference.

The complex aluminosilicates, i.e., zeolite type materials, are useful presoaking/washing adjuvants herein in that these materials soften water, i.e., remove $Ca^{++}$ hardness. Both the naturally occurring and synthetic "zeolites", especially zeolite A and hydrated zeolite A materials, are useful for this builder/softener purpose. A description of zeolite materials and a method of preparation appears in Milton, U.S. Pat. No. 2,882,243, issued Apr. 14, 1959, incorporated herein by reference.

Bleaching compositions of this invention are normally solid thereby facilitating preparation of detergent compositions. The novel bleaches of this invention can be admixed with other granules of optional bleaching or detergent composition materials. Actual particle size of either the bleach-containing granules or optional granules of additional material is not critical. If, however, compositions are to be realized having commercially acceptable flow properties, certain granule size limitations are highly preferred. In general, all granules of the instant compositions preferably range in size from about 100 microns to 3000 microns, more preferably from about 100 microns to 1300 microns.

Additionally, flowability is enhanced if particles of the present invention are of approximately the same size. Therefore, preferably the ratio of the average particle sizes of the bleach-containing granules and optional granules of other materials varies between 0.5:1 and 2.0:1.

Bleaching compositions of the present invention are utilized by dissolving them in water in an amount sufficient to provide from about 1.0 ppm to 50 ppm available oxygen in solution. Generally, this amounts to about 0.0001% to 0.005% by weight of active oxygen in solution. Fabrics to be bleached are then contacted with such aqueous bleaching solutions.

Among the sulfone peroxycarboxylic acids of this invention, the degree of bleaching activity per unit weight of active oxygen can vary widely. Preferred embodiments are those with a relatively high level of bleaching activity per unit weight of active oxygen, since smaller amounts of such compounds can be used to achieve a given degree of bleaching. Embodiments which sustain this high performance at relatively low bleaching temperatures, i.e. $\leq 60°$ C. are particularly preferred. Also preferred are embodiments with a relatively high weight percentage of active oxygen in the sulfone peroxycarboxylic acid molecule, since such embodiments tend to consume a smaller weight of raw materials per unit of active oxygen present.

Thermal and moisture stability of the peroxyacid bleaches are important for safety, storage and shelflife considerations. Many prior art peroxycarboxylic acids that have good bleaching performance have not been commercialized due to poor thermal and moisture stability properties. However, the sulfone peroxyacids of this invention have shown surprisingly high thermal and moisture stabilities.

While the degree of molecular stability (as reflected in such properties as storage stability or thermal stability in various formulations, etc.) will vary among sulfone peroxycarboxylic acids, they are usually more stable than otherwise similar peroxycarboxylic acids which lack the sulfone group. Similarly the tendency to cause dye damage will vary but will usually be reduced by the presence of one or more sulfone groups. Preferred embodiments are those exhibiting relatively high degrees of stability and relatively low degrees of dye damage. Particularly preferred are embodiments which exhibit in a single molecule or reaction product a combination of high stability, low dye damage, and high bleaching activity per unit weight.

Depending upon the specific intended use, such properties as particle size, appearance, and odor of the sulfone peroxycarboxylic acids of this invention may be important. In most embodiments, these compounds can be produced as white, relatively odorless powders of relatively small particle size, and such embodiments are usually preferred. If desired, particle size distribution can be adjusted by such known methods as milling, screening, or agglomeration.

Included within the scope of this invention are various bleaching processes in which sulfone peroxycarboxylic acids are employed in effective amounts as active bleaching ingredients. Generally, in such processes, articles to be bleached are contacted in an aqueous medium with a bleach effective amount of one or more sulfone peroxycarboxylic acids. Other conditions important in such processes include temperature, pH, contact time, selection and level of various ingredients present during bleaching, agitation, etc. Optimization of such conditions can be accomplished for each particular case by routine experimentation in view of this disclosure. Particularly preferred are processes in which the temperature is fairly low, i.e. not above 60° C., since such processes provide rapid and effective bleaching while minimizing adverse effects associated with higher temperatures such as dye damage, fabric shrinkage, high energy consumption, and weakening of fabrics or other articles subjected to bleaching.

Although the invention has been described in terms of specific embodiments which are set forth in considerable detail, it should be understood that this description is by way of illustration only and that the invention is not necessarily limited thereto since alternative embodiments and operating techniques will become apparent to those skilled in the art in view of this disclosure. Accordingly, modifications are contemplated which

What is claimed is:

1. A compound represented by the formula $$A-\overset{\overset{O}{\|}}{\underset{\underset{O}{\|}}{S}}-B$$

wherein A and B are peroxycarboxylic acid compatible organic moieties bonded to the sulfur atom by a carbon atom, each of A and B containing from 1 to 4

$$-\overset{O}{\overset{\|}{C}}-OOH$$

groups bonded to carbon atoms.

2. A compound of claim 1 wherein A and B contain a total of two peroxycarboxylic acid groups.

3. A compound of claim 1 wherein at least one of A and B is an aryl group.

4. A compound of claim 3 wherein the aryl group is a peroxybenzoic acid group.

5. A compound of claim 1 wherein the theoretical active oxygen content is above about 5.42 percent.

6. A compound of claim 1 in the form of a particulate solid.

7. A compound of claim 1 wherein A and B are the same.

8. A compound of claim 1 wherein A and B are dissimilar.

9. A compound represented by the formula $$X-\overset{\overset{O}{\|}}{\underset{\underset{O}{\|}}{S}}-Y$$

wherein X and Y are hydrocarbyl groups, each of X and Y being substituted with a total of from 1 to 4

$$-\overset{O}{\overset{\|}{C}}OOH$$

groups.

10. A compound of claim 9 wherein X and Y are the same.

11. A compound of claim 9 wherein X and Y are different.

12. A compound of claim 9 wherein each of X and Y are aryl.

13. A compound of claim 12 wherein the aryl is phenyl.

14. A compound of claim 9 wherein X and Y are alkyl.

15. A compound of claim 12 wherein each aryl group is the same.

16. A compound of claim 14 wherein the alkyl group has from 1 to 4 carbon atoms.

17. A compound of claim 14 wherein the alkyl is ethyl.

18. A compound of claim 11 wherein X is alkyl having from 9 to 12 carbon atoms and Y is alkyl having from 1 to 4 carbon atoms.

19. A compound of claim 9 wherein X is cyclohexyl and Y is ethyl.

20. A compound of claim 9 wherein X is methyl and Y is phenyl.

21. A compound of claim 9 wherein X and Y are peroxybenzoic acid groups.

22. A compound of claim 9 wherein X is an alkyl group and Y is a peroxybenzoic acid group.

23. A compound of claim 22 wherein the alkyl group contains from 2 to 10 carbon atoms.

24. A compound of claim 23 wherein the alkyl group is ethyl.

25. A bleaching detergent composition comprising an effective amount of a compound of claim 1 and a detergent surfactant.

26. A composition of claim 25 further including a detergent builder.

27. A composition of claim 25 wherein the surfactant is selected from anionic, nonionic and zwitterionic surfactants.

28. A composition of claim 25 wherein A or B are independently selected from the group consisting of a cyclic, linear or branched alkyl group, an aryl group, an alkylaryl group, an aromatic heterocyclic group, a polyaryl group consisting of from 2 to 4 annelated enzenoid rings, and mixtures thereof containing up to about 18 carbon atoms and being optionally additionally substituted with halogen, sulfonate, nitro, carboxylate, carboxylic acid, $C_{1-5}$ alkyl, hydroyx, trifluoromethyl, aryl, sulfone, amine oxide, amide, ester or sulfate groups, or mixtures thereof.

29. A composition of claim 25 wherein A and B are the same.

30. A composition of claim 25 wherein A and B are dissimilar.

31. A composition of claim 25 wherein A and B contain a total of two $$-\overset{O}{\overset{\|}{C}}-OOH$$

groups.

32. A composition of claim 25 wherein A is an alkyl group and B is an aryl group.

33. A bleaching detergent composition comprising an effective amount of a compound of claim 9 and a detergent surfactant.

34. A composition of claim 33 wherein X and Y are the same.

35. A composition of claim 33 wherein X and Y are different.

36. A composition of claim 33 wherein each of X and Y are aryl.

37. A composition of claim 36 wherein the aryl is phenyl.

38. A composition of claim 33 wherein X and Y are alkyl.

39. A composition of claim 37 wherein each aryl group is the same.

40. A composition of claim 38 whereien the alkyl group has from 1 to 4 carbon atoms.

41. A composition of claim 38 wherein the alkyl is ethyl.

42. A composition of claim 35 wherein X is alkyl having from 9 to 12 carbon atoms and Y is alkyl having from 1 to 4 carbon atoms.

43. A composition of claim 33 wherein X is cyclohexyl and Y is ethyl.

44. A composition of claim 33 wherein X is methyl and Y is phenyl.

45. A dry bleach composition comprising, by weight, from about 0 percent to about 50 percent detergent surfactant, detergent builder or a mixture thereof and from about 1 percent to about 50 percent of a compound of claim 1.

46. A dry bleach composition comprising, by weight, from about 0 to about 50 percent detergent surfactant, detergent builder or a mixture thereof and from about 1 percent to about 50 percent of a compound of claim 9.

47. A process for bleaching articles comprising contacting articles to be bleached with an aqueous medium containing a bleach effective amount of a compound represented by the formula:

wherein A and B are peroxycarboxylic acid compatible organic moieties bonded to the sulfur atom by a carbon atom, each of A and B containing at least one

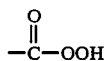

group bonded to carbon atoms.

48. A process of claim 47 wherein A and B are the same.

49. A process of claim 47 wherein A and B are dissimilar.

50. A process of claim 47 wherein A and B contain a total of two

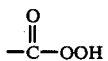

groups.

51. A process of claim 47 wherein A is an alkyl group and B is an aryl group containing at least one

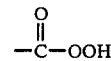

group.

52. A process for bleaching articles comprising contacting articles to be bleached with an aqueous medium containing a bleach effective amount of a compound represented by the formula:

wherein X and Y are hydrocarbyl groups, each of X and Y being substituted with at least one

group.

53. A process of claim 52 wherein X and Y are the same.

54. A process of claim 52 wherein X and Y are different.

55. A process of claim 52 wherein each of X and Y are aryl.

56. A process of claim 52 wherein the aryl is phenyl.

57. A process of claim 52 wherein X and Y are alkyl.

58. A process of claim 57 wherein the alkyl group has from 1 to 4 carbon atoms.

59. A process of claim 58 wherein the alkyl is ethyl.

60. A process of claim 54 wherein A is alkyl having from 9 to 12 carbon atoms and B is alkyl having from 1 to 4 carbon atoms.

61. A process of claim 52 wherein X is cyclohexyl and Y is ethyl.

62. A process of claim 52 wherein X is methyl and Y is phenyl.

* * * * *